United States Patent
Evensen et al.

[11] Patent Number: 5,890,802
[45] Date of Patent: Apr. 6, 1999

[54] PIEZO-CERAMIC ACTUATOR-DRIVEN MIXING DEVICE

[75] Inventors: Harold T. Evensen, Seattle; David L. Cunningham, Kirkland, both of Wash.

[73] Assignee: University of Washington, Seattle, Wash.

[21] Appl. No.: 26,987

[22] Filed: Feb. 20, 1998

Related U.S. Application Data

[60] Provisional application No. 60/039,022 Feb. 21, 1997.

[51] Int. Cl.$^6$ ........................................... B01F 11/02
[52] U.S. Cl. ............................................... 366/127
[58] Field of Search .................... 366/127, 130, 366/208, 348, 349; 422/99, 100, 104; 436/174, 179, 180

[56] References Cited

U.S. PATENT DOCUMENTS

| | | |
|---|---|---|
| 2,219,348 | 10/1940 | Turner, Jr. . |
| 3,591,862 | 7/1971 | Winston . |
| 3,715,104 | 2/1973 | Cottell . |
| 4,118,797 | 10/1978 | Tarpley, Jr. ............................. 366/127 |
| 4,960,566 | 10/1990 | Mochida . |
| 5,395,592 | 3/1995 | Bolleman et al. ...................... 366/127 |

*Primary Examiner*—Charles E. Cooley
*Attorney, Agent, or Firm*—Delbert J. Barnard

[57] ABSTRACT

A device and method for mixing an aspirated fluid slug (40), such as a DNA sample and reagent, within a capillary tube (28) through the electrical deflection of a diaphragm, such as a piezo-ceramic disk (12). The device (10) includes first and second mounting plates (16, 18). The piezo-ceramic disk (12) is sandwiched between two O-rings seals (14) and the two mounting plates (16, 18) to form an air seal (21) between the disk (12) and the first mounting plate (16). A first opening (24) receives an end (26) of the capillary tube (28) and extends almost completely through the first mounting plate (16) such that the end (26) is essentially perpendicular and adjacent to the disk (12). A smaller axially-aligned second opening (30) connects the air seal (21) between the disk (12) and the first mounting plate (16) to dead air volume (42) in the capillary tube (28). A third O-ring seal (34) seals the capillary tube (28) to the first mounting plate (16) at the first opening (24). A power source (44) applies a voltage to the disk (12) to produce a deflection of the disk. The deflection acts on the sealed dead air space between the disk (12) and dead air volume (42) to rapidly move the fluid slug (40) back and forth within the capillary tube (28).

21 Claims, 3 Drawing Sheets

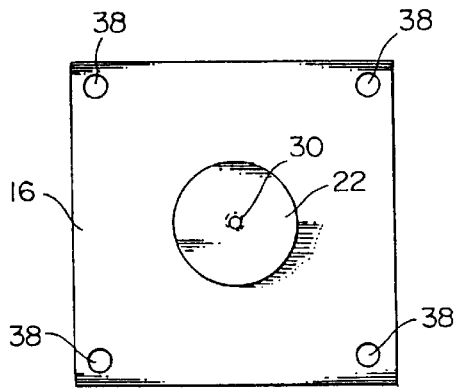
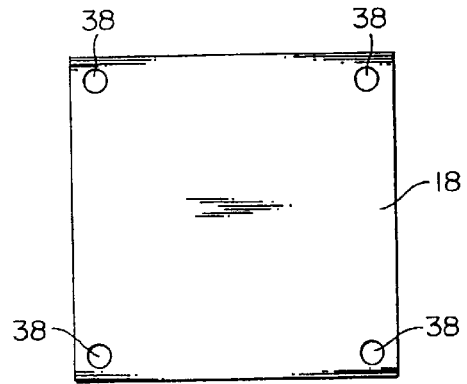
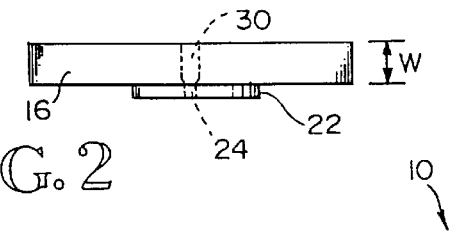
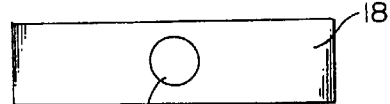
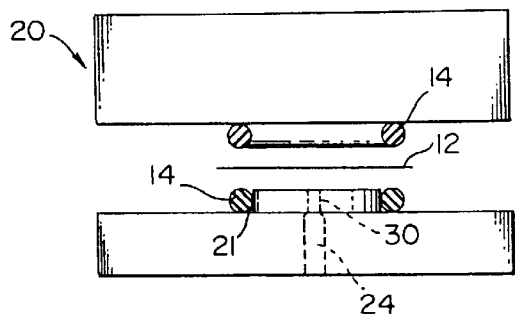
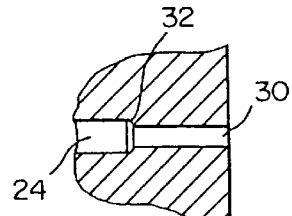
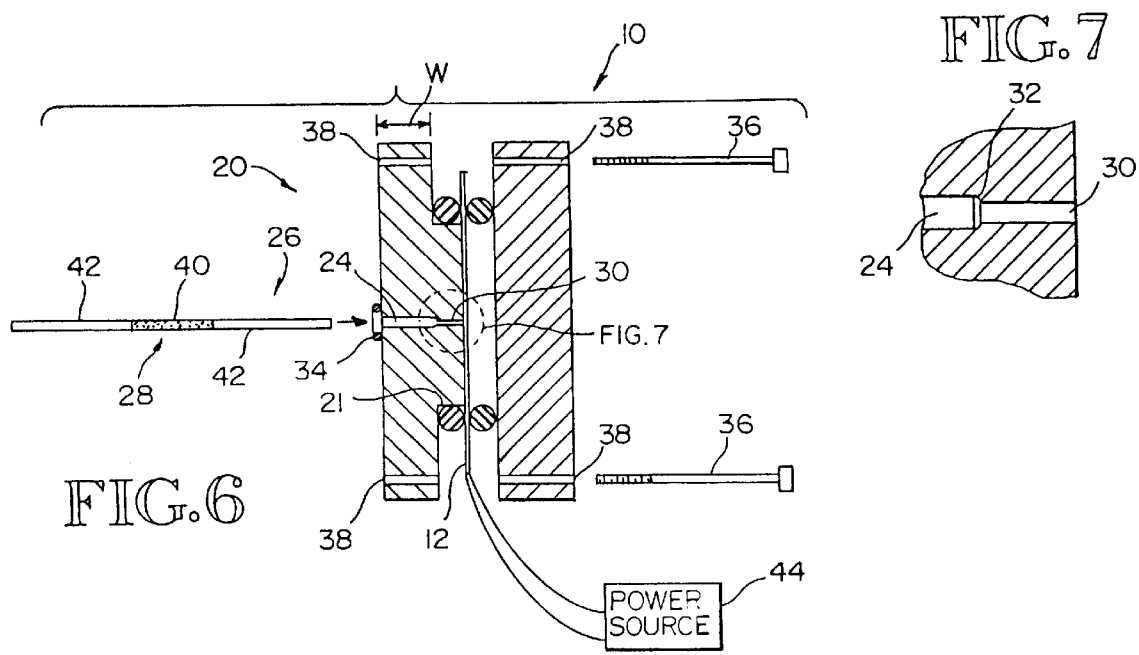

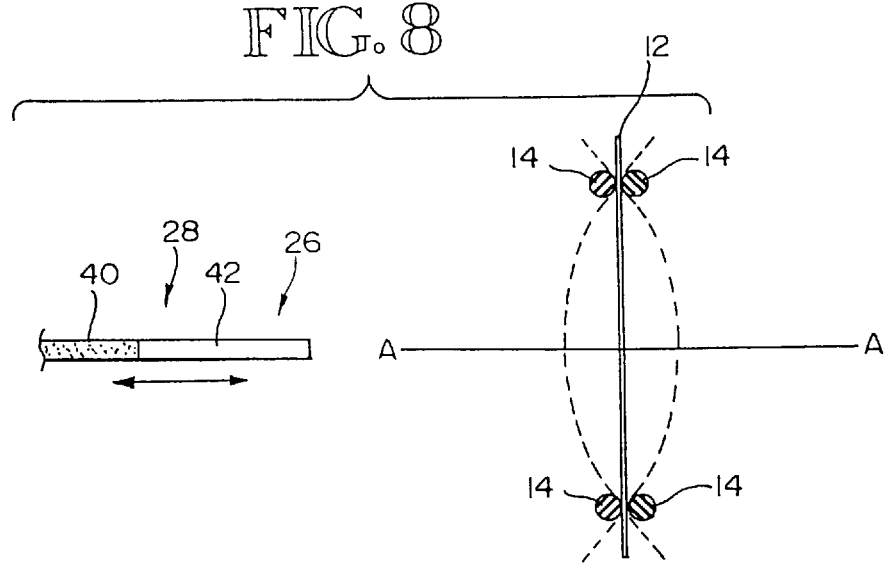
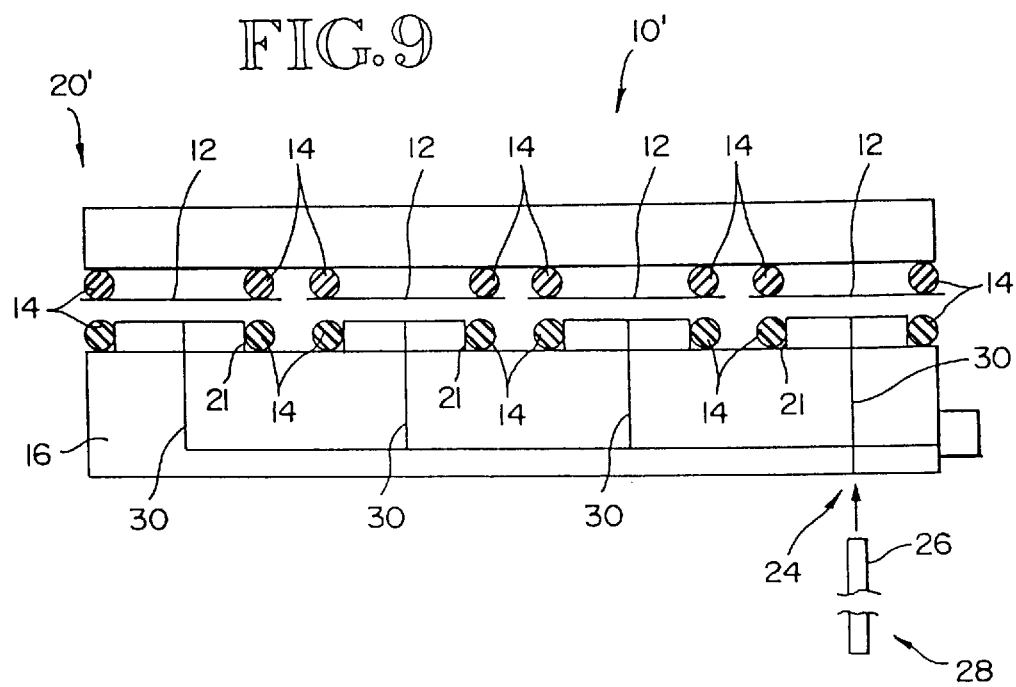

PIEZO-CERAMIC ACTUATOR-DRIVEN MIXING DEVICE

STATEMENT OF INTEREST

This application was based on research that was funded in cooperation with NIH grant No. 1 RO1 HG01497-01. As such, the United States Government may have rights to this invention.

RELATED APPLICATIONS

This application claims priority to provisional application Ser. No. 60/039,022, filed Feb. 21, 1997.

TECHNICAL FIELD

The present invention relates to a mixing device and method for mixing a fluid sample aspirated within a dead air volume all within a tubular member, such as a glass capillary tube. More specifically, the present invention relates to a mixing device apparatus having a mounting frame that can receive an end of a aspirated fluid capillary tube, wherein the frame includes a piezo-ceramic disk containing piezo elements that asymmetrically deflect when a voltage is applied to the disk. The end of the capillary tube is air sealed adjacent the piezo-ceramic disk such that the fluid within the capillary tube moves back and forth to become a homogenous mixture and expels dead air volume within the tube during resonation of the piezo element.

BACKGROUND OF THE INVENTION

Glass capillary tubes with an inner diameter of less than 1 mm are often used to handle small, sub-microliter fluid volumes in chemistry and biology. With the advent of advanced gene sequencing research, automated systems are used to prepare a large number of small, sub-microliter samples in a relatively short period of time (e.g. 5,000 samples in eight hours). For small fluid volumes, a long visible fluid sample (also called a slug) is aspirated into a capillary tube encased within dead air volume. The aspirated fluid within the dead air volume is more easily handled, observed, and controlled by a researcher/technician. Often, the capillary tubes themselves become individual reaction chambers in which solution containing DNA, or other sampled material is combined with a plurality of reagents. The aspirated fluid must be mixed and the air bubbles removed before the resulting mixture is ready to be incubated or thermal cycled, depending on the reaction of interest.

Traditionally, small volumes have been mixed in biochemistry laboratories through hand-pipetting one sample into a container holding another mixture. The turbulence as the fluid enters and leaves the nozzle tip of the hand-pipette and the large exposed surface area between the fluids allows mixing to progress quickly. However, this method is labor intensive, not conducive to automation, and risks losing sample to the outer surface of the capillary tube from surface tension.

In automated processes, the known mixing options are limited. The mixing time in automated systems needs to be relatively quick, for example, mixing one microliter water solution within three seconds. Previously-known mixing devices include a precision linear actuator, which is coupled to the capillary tube by an O-ring that is used to move the fluid. However, precision linear actuators are expensive and bulky. Additionally, the speeds obtained through precision linear actuators are limited to approximately 200 mm per second or mm/sec. Some commercial units can move over 1 mm/sec., but the response time of a particular fluid slug can be limiting. Another limitation with piston-drive actuators is that the system can become overheated due to friction between the piston and the O-ring. This friction can negatively affect system reliability and reduce the allowable mixing envelope.

Another known mixing method within an automated system is disclosed in Mochida, U.S. Pat. No. 4,960,566, granted Oct. 2, 1990 and entitled, "Chemical Reaction Apparatus." Mochida discloses the use of capillary action to fill the entire capillary with fluid. Mochida discloses injecting a wash solution and expelling it out to achieve mixing. This process requires more time to cycle through the automated system disclosed in Mochida. Also, the system does not allow for the visibility of the fluid slug, which is desirable because of the ability to easily handle, observe and control the slug.

It is an object of the present invention to completely mix sub-microliter volumes that are aspirated between dead air volumes within the chamber of a capillary tube, and that such device be amenable to incorporation into a high-speed automation process.

DISCLOSURE OF THE INVENTION

The present invention relates to an apparatus and method for mixing aspirated fluid within a capillary tube. This apparatus and method is particularly amenable to automated biochemical fluid sampling processes.

The device of the present invention includes a mounting frame having a first mounting plate and a second mounting plate. A diaphragm, such as a piezo-ceramic disk, is positioned between two seals in order to sandwich the diaphragm between the first and second mounting plates. Thus, an air seal is formed between the diaphragm and at least the first mounting plate. The first mounting plate includes a first opening of a size to receive an end of the aspirated fluid capillary tube such that the received end is essentially perpendicular and adjacent the diaphragm. A second smaller and axially-aligned opening connects the air seal between the diaphragm and the first mounting plate and the end of the capillary tube. The device also includes a power source to apply voltage to the diaphragm. In use, the end of the aspirated fluid capillary tube is received into the first opening of the first mounting plate such that the fluid adjacent the received end of the capillary tube is sealed with the air seal of the diaphragm and the first mounting plate. A voltage is applied to the diaphragm to cause deflection of the diaphragm such that the deflection acts on the sealed air, which, in turn, moves the fluid within the capillary tube back and forth such that the fluid is mixed in a matter of seconds.

In preferred form, the seal is an O-ring.

According to an aspect of the present invention, the first opening to receive the end of the aspirated fluid capillary tube extends almost the entire width of the first mounting plate, thereby creating an abutment within the mounting plate to restrain the received end of the capillary tube. The second opening extends axially of the first opening through the remainder of the width of the first mounting plate to join the air seal between the diaphragm and the first mounting plate to the fluid within the capillary tube.

In preferred form, a third seal seals the capillary tube around the first opening.

According to another embodiment of the present invention, a pressure relief valve may be added to the device, which is vented into the air sealed space between the diaphragm and the received end of the capillary tube to further externally control the pressure within the capillary tube during mixing. Another embodiment includes a separate external control system including a three-way valve and a shut-off valve venting into the air-sealed space between the diaphragm and the received end of the capillary tube in order to channel and direct the air-sealed space between the diaphragm and a shut-off valve.

In yet another embodiment of the present invention, the device includes a protrusion extending upwardly from the mounting plate within the space between the first mounting plate and the second mounting plate. The protrusion is of a size to receive one of the O-ring seals in order to better seal the air space between the diaphragm and the first mounting plate and to position the second opening closer to the diaphragm.

In yet another embodiment, the present invention allows for improved fluid displacement within the capillary tube through a device that includes a frame containing a plurality of parallel diaphragms, each within a pair of seals. Each diaphragm includes its own perpendicularly vented second opening wherein each second opening is commonly vented into the received end of the capillary tube.

The present invention also includes a method of mixing aspirated fluid within a capillary tube. The method includes the steps of providing a capillary tube containing an aspirated fluid slug encased in dead air volume. The next step includes providing a diaphragm deflecting mixing device, having a diaphragm, which is air sealed within a mounting frame. The mounting frame includes an opening of a size to receive an end of the aspirated fluid capillary tube that is essentially perpendicular and adjacent the diaphragm. The next step includes inserting the capillary tube into the diaphragm deflecting mixing device such that the dead air volume of the received end becomes connected and sealed to the sealed air between the diaphragm and the capillary tube end. The next step includes applying voltage to the diaphragm such that the diaphragm deflects to displace the dead air volume within the received end of the capillary tube. The fluid slug within the capillary tube rapidly is moved back and forth by the displaced air volume to mix the fluid slug within a matter of seconds.

These and other advantages, objects and features will become apparent from the following best mode description, the accompanying drawings, and the claims, all of which are incorporated herein as part of the disclosure of the invention.

BRIEF DESCRIPTION OF THE DRAWINGS

Like reference numerals are used to designate like parts throughout the several views of the drawing, wherein:

FIG. 1 is a back view of a first mounting plate of the mounting frame and showing a circular protrusion protruding generally centrally of the plate of a size to receive an O-ring; and an opening to receive an end of a capillary tube extending partially through the width of the first mounting plate with a smaller opening extending the rest of the width of the plate;

FIG. 2 is a plan view of the first mounting plate of FIG. 1;

FIG. 3 is a front view of the second mounting plate of the mounting frame;

FIG. 4 is a plan view of the second mounting member of FIG. 3 and showing a tapped hole at one end of the second mounting plate for connection to a mechanical support and/or an automation system and the like;

FIG. 5 is an end view of the mounting frame (shown rotated 90 degrees) with a diaphragm, such as a piezo-ceramic disk, positioned between a pair of O-rings (shown in section) and the first and second mounting plates;

FIG. 6 is a sectional end view of the mounting frame and connectors to connect the first and second plates, with the piezo-ceramic disk sandwiched between the two O-rings and two mounting plates, and with an aspirated capillary tube with a fluid slug encased in dead air volume about to be received into the opening in the first plate essentially perpendicular to the piezo-ceramic disk, and schematically showing a power source connected to the piezo-ceramic disk;

FIG. 7 is an enlarged detail view taken substantially along circle seven of FIG. 6 better showing the opening to receive the end of the capillary tube, which extends through most of the width of the first mounting plate and showing a smaller diameter hole that is axially aligned with the opening end that is drilled through the remainder of the first mounting plate to complete the air seal and form an abutment to the end of the capillary tube;

FIG. 8 is a schematic view showing the exaggeratedly asymmetric/azimuthal deflection pattern that the piezo-ceramic elements of the piezo-ceramic disk make when a voltage is applied to the disk and showing the movement of a fluid slug and dead air volume within the capillary tube;

FIG. 9 is an end view of an alternate embodiment of the present invention for increasing the net throw volume of the samples through a plurality of small drilled holes and additional parallelly-aligned piezo-ceramic disks and corresponding O-rings;

BEST MODE FOR CARRYING OUT THE INVENTION

Figure 10:
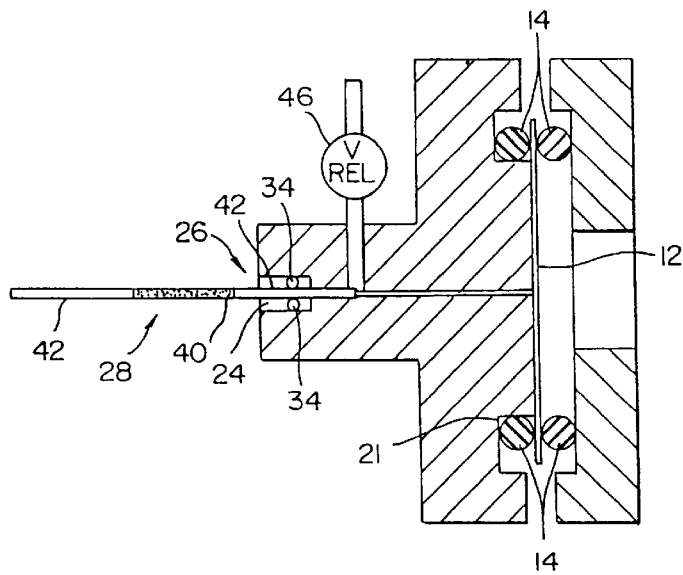
FIG. 10 is an end view, similar to that of FIG. 6 and also disclosing a vent valve to control aspirated volume within the capillary tube.

The present invention relates to a piezo-ceramic actuator-driven mixing device and method for mixing fluid slugs within capillary tubes. A primary purpose of the present invention is to provide a compact, inexpensive, easy to control device in order to mix fluids within the capillary tube to obtain a high-throughput capillary-based reaction.

Referring to FIGS. 1–5, the mixing device 10 of the present invention includes a diaphragm capable of electrical deflection, such as a piezo-ceramic crystal/disk 12, (FIGS. 5 and 6) that is sandwiched between two O-rings 14, which are, in turn, held between a first mounting plate 16 and a second mounting plate 18 of a mounting frame 20. The blocks are squeezed together to form a pressure (air) seal 21 around the piezo-ceramic disk 12. The O-rings are the seals to form the air seal 21 between the first mounting plate and the disk.

The piezo-ceramic disk is a thin brass disk that is coated on at least one side with a piezo-ceramic coating (the piezo element). In preferred form, the piezo-ceramic coating is on both sides of the thin brass disk. Applications of voltages to the piezo elements cause a change in their size due to a piezo electric effect. The piezo-ceramic disk is similar to elements used in some "tweeter" high-frequency speakers, such as Motorola Part No. KSN1005A. A small voltage differentiation applied to the coatings will result in an asymmetric deflection, which can be surprisingly fast, such as in the range of 1–2 kH.

Referring again to FIG. 1, the first mounting plate 16 may also include a circular protrusion 22 positioned generally centrally of the plate. This protrusion is of a size to accept one O-ring 14. The device itself is compact, such that a 1/32 inch I.D. O-ring may be used. The benefit of this feature will be further discussed below.

Referring to FIG. 4, an aperture 25, such as a tapped hole, may be made at one end of the second mounting plate 18 in order to be connected to a mechanical support and/or part of an automation processor.

Referring also to FIGS. 6 and 7 a first opening 24 of a size to receive an end 26 of a capillary tube 28 is drilled most of the way through the width w of first mounting plate 16 and substantially perpendicular to the piezo-ceramic disk 12. Hereinafter, the term "perpendicular to the piezo-ceramic disk" (or diaphragm in the claims) is broadened to include mechanical set offs that would place the capillary tube ultimately perpendicular to the piezo-ceramic disk.

A second, smaller opening 30, which is axially-aligned to the first opening 24, is drilled the rest of the way through the width w of mounting plate 16. For example, the second opening 30 may be on the order of the inner diameter of the capillary tube. This second opening connects into the sealed air 21 between the piezo-ceramic disk and the first mounting plate. The differential between the first opening and second opening creates an abutment 32 to a received capillary tube end 26. In this manner, the air seal 21 is now an enlarged air seal between the capillary tube end 26 (when inserted into opening 24) and the piezo-ceramic disk 12.

A third seal 34 is also preferably positioned around capillary tube 28 where it enters first opening 24 such that the differential in atmospheric pressure is less than $0.1_{ATM}$. In preferred form, this third seal 34 is also a small O-ring. However in automated systems, the third seal may be part of a balloon gripper (not shown), which seals, inserts, and extracts the capillary tube to and from the device.

The two mounting plates 16, 18 are connected to each other through a plurality of connectors 36, where the O-rings 14 and the piezo-ceramic disk 12 are sandwiched between the two plates 16, 18. The connectors 36 may be long bolts such as shown in FIG. 6, which are received through a plurality of apertures 38, where one aperture is in each corner of each mounting plate.

Each capillary tube 28, as part of a small volume biochemical sampling process, includes a fluid 40 (also called a "slug"), such as DNA and a reagent, that ultimately will be mixed within the capillary tube chamber. Because it is desired to visibly see and control the fluid, the fluid slug is encased between dead air volume 42 during the aspiration process.

A power source 44 provides voltage to the piezo-ceramic disk 12 in order to cause the disk to exaggeratedly azimuthally deflect about plane A—A, which is essentially perpendicular and passes through piezo-ceramic disk 12, as shown in FIG. 8. The actual deflection is asymmetrical, however. The piezo-ceramic disk is preferably driven in a sawtooth wave form in a range of 50–200 V peak-to-peak. Use of a sawtooth waveform allows good control over the fluid velocity. AC operation as opposed to DC operation, prevents overdriving the piezo components and depolarizing the crystal.

When the piezo-ceramic disk is activated, the disk bends (deflects), as exaggeratedly shown in FIG. 8, displacing trapped dead volume air 42 between the piezo-ceramic disk and the fluid 40 in the adjacent and substantially perpendicular capillary tube 28. The fluid moves in order to return the dead volume air pressure to that of the surrounding atmosphere.

Rapid mixing of the different fluids is achieved through diffusion between a main fluid volume in the capillary and a thin fluid film it deposits on the capillary wall through its motion. Air bubbles in the fluid are processed out of the capillary tube by use of the deflection of the piezo-ceramic disk. The mixing time is found to be inversely proportional to the fraction of the fluid volume left in the film layer for each cycle. The mixing time is therefore controlled by the dead air volume of the system, the fluid volume, the capillary tube size, and the displacement limits of the piezo-ceramic device, in addition to the intrinsic properties of the fluid being mixed.

In testing, the device has been found to mix two 1 $\mu l$ water solution in under three seconds.

In order to better understand and optimize the mixing process, an analysis model was developed to describe pressure-driven fluid motion in a capillary tube. The capillary tube is assumed to be sealed at one end and open at the other end. The pressure at the sealed end is controlled by displacing the trapped dead air volume with the piezo-ceramic actuator. This means of controlling the pressure via volume displacement is referred generically as a piston. The purpose of this model is to understand the mixing mechanism sufficiently so that it may be optimized. Therefore, various simplifications are made and justified during its development. The motion of the fluid volume is described as follows in relationship to FIG. 12. The displacement of the piston and the motion of the fluid volume can be represented by $x_1$ and $x_0$, respectively. At the initial condition, the dead volume is that which is between the boundaries marked by the fluid meniscus and piston. Using this representation $V_{dead} = \pi R^2 (x_1 - x_0)$ and $Q = \pi R^2 \dot{x}_1$, where Q is the volume flow rate and R is the capillary radius. The force balance equation for the fluid volume in a horizontal capillary is:

$$M_f \ddot{x}_1 = (P_{dead} - P_{atm}) \pi R^2 - 2eRL\tau, \quad (1)$$

where the driving term for the pressure gradient and the drag therm from viscous effects are shown. In Eq. (1), $m_f$ is the fluid mass, $P_{dead}$ is the pressure of the dead volume, $P_{atm}$ is atmospheric pressure, R is the capillary inner radius, L is the total length of the fluid volume in the capillary which can include small enclosed bubbles, and r is the wall shear stress for the fluid flow. It has been assumed that the air at the open end of the capillary is at atmospheric pressure, and internal air flow resistance is neglected. The air flow resistance may be neglected because the viscosity of air ($1.8 \times 10^{-5}$ Ns/m$^2$) is about 50 times less than that of water ($1 \times 10^{-3}$ N s/m$^2$); the pressure drop along the air column is only comparable to that along the fluid column if it is 50 times longer than the fluid column.

Figure 12:
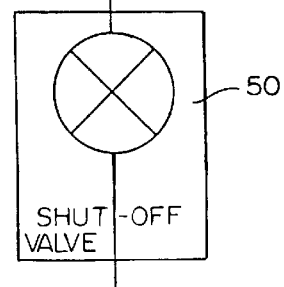
FIG. 12 is a schematic view of a piezo actuator analysis model for better describing the process that is taking place during piezo action upon the fluid slug in the capillary tube.

The relationship between the shear stress and the fluid velocity is $r = \mu(du/dr)$, where u is the laminar radial velocity profile [$u = u(r,t)$] and the shear stress is evaluated at the capillary wall. This is not constant, as the radial velocity profile changes as the fluid volume undergoes its motion. The exact solution of u (r,t) can be found by solving the Helmholtz equation in cylindrical geometry:

$$\frac{\partial u}{\partial t} - v\left(\frac{\partial^2 u}{\partial r^2} + \frac{1}{r}\frac{\partial u}{\partial r}\right) = -\frac{1}{p}\frac{dp}{dx}, \quad (2)$$

where v is the kinematic viscosity, p is the fluid density, and dp/dx is the pressure that drives the fluid motion. This pressure is assumed to jump instantaneously with the piezo motion, decrease as the fluid volume moves, and has the form $$-\frac{dp}{dx} = \frac{P_{aim}}{L} \frac{[V_{piezp} - \int Q(t)]/\pi R^2}{x_{10} + [\int Q(t) - V_{piezp}]/\pi R^2}, \quad (3)$$

where $\int Q(t)$ is the cumulative volume flow, $V_{piezo}$ is the volume displacement of the piezo, and $x_{10}$ denotes the initial position of the fluid volume, again using the notation of FIG. 12. This can be simplified before substitution into Eq. (2) by making the approximation that the denominator is approximately constant in time and equal to $(X_{10}-X_{00})=V_{dead}/\pi R^2$, where $x_{00}$ represents the position of the fluid meniscus and driving piston before the piezo motion begins. For the present system, this assumption introduces error of less than 10% since the maximum piezo displacement is on the order of 3 $\mu$l in a system with over 30 $\mu$l of dead volume. By expanding the expression for $\int Q(t)$ as $2\pi \int_0^R \int_0^t u(R,t)$, Eq. (2) is brought to a form which has been solved elsewhere;

$$\frac{\partial u}{\partial t} - v\left(\frac{\partial^2 u}{\partial r^2} + \frac{1}{r}\frac{\partial u}{\partial r}\right) = \frac{P_{aim}V_{piezp}}{\rho L V_{dead}} - \frac{2\pi P_{aim}}{\rho L V_{dead}} \iint u(r,t) r dr dt. \quad (4)$$

The solution to Eq. (4) is a function of zero-order Bessel functions of the first kind, $J_0$. For the parameters used here, the radial profile of u (r,t) changes only slightly with time, and is close (always within 15%) to the parabolic velocity profile of Hagen-Poiseuille fully developed laminar flow. Therefore, for simplicity, the Hagen-Poiseuille wall shear stress and flow rate are employed in Eq. (1):

$$Q = \pi \times \Delta P \times R^4 / 8\mu L, \quad (5)$$

$$\tau = R \times \Delta P / 2L = 4\mu Q / \pi R^3, \quad (6)$$

The volume flow rate Q is replaced in Eq. (6) with $\pi R^2 x_1$ before substitution into Eq. (1).

By treating the dead volume as an ideal gas at constant temperature, the pressure term in Eq. (1) can be replaced with $$P_{dead} - P_{aim} = \frac{P_{aim}(x_{10} - x_{00})\pi R^2}{(x_1 - x_0)\pi R^2} - P_{aim} \quad (7)$$

As was done with Eq. (3), this can be simplified to within 10% accuracy by setting the denominator equal to the initial value, $(x_{10}-x_{00})$. Substituting Eq. (7) into Eq. (1), using $m_f = P\pi R^2 L$ and redefining the displacements $x_1$, and $x_0$ as displacement about their initial value leads to a second-order linear differential equation:

$$\ddot{x}_1 + \frac{8\mu}{\rho R^2}\dot{x}_1 + \frac{P_{aim}\pi R^2}{V_{dead}\rho L} = \frac{P_{aim}\pi R^2}{V_{dead}\rho L}x_0. \quad (8)$$

Taking the Laplace transform of this equation, the frequency response of the fluid volume position $X_1$ (s) to the piston motion $X_0$ (s) follows as $$\frac{X_1(s)}{X_0(s)} = \frac{\omega_n^2}{s^2 + 2\zeta\omega_n s + \omega_n^2}, \quad (9)$$

where $$\omega_n = \frac{P_{aim}\pi R^2}{V_{dead}\rho L}, \quad \zeta = \frac{4\mu}{R^3}\sqrt{\frac{V_{dead}L}{P_{aim}\pi\rho}}. \quad (10)$$

This formulation is very useful in that the fluid motion response to any input function can be found by using standard techniques to analyze linear systems. In addition, the frequency response of the fluid motion is easily found. The bandwidth, $\omega_{BW}$ or the frequency at which the square of the amplitude of the fluid slug motion is one half of the low frequency response is $$\omega_{BW}^2 = \omega_n^2(1-2\zeta^2 + \sqrt{(2\zeta^{2-1})^2+1}). \quad (11)$$

Therefore, to attain a large range of fluid motion with a fixed driving amplitude at high frequency $\zeta^2$ should be minimized and $\omega_n^2$ should be maximized. This can be done by reducing the dead volume and the fluid volume or by using a capillary with a larger inner diameter. A time constant associated with this bandwidth can be defined as $\tau_{BW} = 2\pi/\omega_{BW}$.

When a viscous fluid moves over a hydrophilic surface, it leaves behind a thin coating film. In an enclosed channel such as a capillary, this causes an entrapped bubble to travel faster than its surrounding fluid because the bubble has a volume flow rate equal to that of the fluid while moving within an effectively smaller channel due to the coating film. By equating the volumetric flow rates of the bubble and the fluid, one finds $$\frac{V_f}{V_b} = \left(1 - \frac{b}{R}\right)^2 \equiv 1 - W, \quad (12)$$

where $V_f$ and $V_b$ are the fluid and bubble velocities, b is the film thickness, and W is defined so that the bubble speed exceeds the fluid speed by an amount $Wv_b$. Parameter W has been liked both theoretically and experimentally to the capillary number, $Ca \equiv \mu V_f/\sigma$, which represents the relative strengths of viscous and surface tension effects. It was found experimentally that for water with capillary numbers up to 0.004 (and flow speeds to 0.3 m/s), $$W \cong \sqrt{Ca}. \quad (13)$$

This relation was found to hold for capillary numbers up to 0.1 for more viscous solutions. For a film thickness much smaller than the capillary inner radius, Eq. (12) and (13) can be combined to yield $$\frac{b}{R} \cong \frac{1}{2}\sqrt{Ca} = \frac{1}{2}\sqrt{\frac{\mu V_f}{\sigma}}. \quad (14)$$

Bubble procession in mixing occurs by virtue of the difference between the bubble velocity and the fluid velocity given in Eq. (12), which results from the nonlinear relationship between the thickness of the coating film and the fluid velocity given in Eq. (14). If the fluid in a capillary is made to move cyclically such that its velocity is higher in one direction than the other, the bubble will have a small net velocity in the direction of the higher fluid velocity.

Using Eq. (12), the net distance covered by the bubble in one cycle is $$\Delta b_1 - \Delta b_2 = \Delta x \left( \frac{1}{1-W_1} - \frac{1}{1-W_2} \right) \quad (15)$$

$$= \Delta x \frac{(W_1 - W_2)}{(1-W_1)(1-W_2)}$$

where $\Delta x$ is the distance that the fluid volume moves within the capillary, using the model of FIG. 12, and the numerical subscript refers to one of the two directions of fluid motion. Bubble procession thus depends on the asymmetry of $W_1$ and $W_2$ as well as the throw distance. The fastest bubble procession can be found by maximizing the bubble procession per unit time. The time per cycle is $\Delta x(V_{f1}^{-1}+V_{f2}^{-1})$, so using the definition of Ca to substitute for the fluid velocity and Eq. (12) to substitute W for Ca, we find $$\frac{\Delta b_1 - \Delta b_2}{2\Delta t} = \frac{(W_1 - W_2)}{(1-W_1)(1-W_2)} \frac{W_1^2 W_2^2}{(W_1^2 + W_2^2)} \frac{1}{(\mu/\sigma)} \quad (16)$$

The maximum bubble procession speed depends on the values of $W_1$ and $W_2$. In systems in which water is the working fluid and maximum fluid velocities are between 0.5 and 2 m/s, the optimum ratio of the two velocities is between 2.4 and 2.8.

It was found experimentally that a slight modification to Eq. (15) is needed for very large air bubbles; therefore $\Delta x$ should be replaced by the greater of:

$$\Delta x - \delta 1 \text{ or } 0,$$

where $\Delta x$ is the throw distance and $\delta 1$ is the bubble length. This effect can be described as the bubble having to completely enter a section of the capillary with the thin film for the procession to occur: in other words, the throw distance must be larger than the bubble size. In turn, Eq. (16) must be modified by replacing the unity term in the numerator with the greater of:

$$1 - \frac{\delta l}{\Delta x} \text{ or } 0,$$

and the bubble procession rate improves as the throw distance $\Delta x$ is increased.

The bubble procession speed is thus optimized by driving the fluid in one direction at the highest velocity possible, and making the slower velocity in the other direction roughly 35%–40% of this. The throw distance must be made as many times larger than the bubble size as possible. To enhance mixing, the throw distance should be greater than or equal to one half the total length of the fluid and air volumes. This ensures that both ends of the fluid volume can mix directly with fluid from the center of the fluid volume via the film on the capillary wall.

Note that the stated optimal velocity ratio is the actual velocity of the fluid, not the velocity of the driving piston. If the time for the piston to go from its minimum position to its maximum position is comparable to or smaller than the time constant $\tau_{BW}$ defined above, then the water volume lags the piston and the system is unable to keep up with the input. In this case, the net fluid velocity will be much less than the piston velocity and a higher input velocity ratio will be needed to approach the ideal fluid velocity ratio. For example, a system with a large dead volume could require a piston velocity ratio in the range of 5–10:1 to achieve optimal procession at a fluid velocity ratio of 2.7:1.

Optimizing the bubble procession rate thus depends not only on maximizing the throw distance (piezo displacement volume) but also on minimizing the time constant. The throw distance is limited by the capabilities of the actuator, so as with mixing it is advantageous to reduce the dead volume as much as possible.

In testing, the following data was obtained Table 1

| Trial No. | Total number of cycles ($\times 10^6$) | Throw distance (mm) |
| --- | --- | --- |
| 1 | 10 | 20.0 |
| 2 | 16.7 | 12.0 |
| 3 | 46.7 | 11.7 |

The present invention is envisioned to be part of an automated process, as such the invention's inherent compactness and ease of use is ideally situated to such automated processes. As already discussed above, the O-ring seal 34 may be replaced with a balloon gripper (not shown) that inserts and seals the capillary tube into the first mounting plate.

Referring to FIG. 9, an alternate embodiment 10' of the present invention can accommodate increased fluid displacement (throw distance), if required, by having a single mounting frame 20' housing, a plurality of piezo-ceramic disks 12 with O-rings 14 to form a pressure seal 21 in parallel to each. A plurality of individual second openings 30, each leading to a corresponding piezo-ceramic disk 12 are vented to the first opening 24 that receives the capillary tube end 26. The additional piezo elements will cause greater asymmetric deflection, which in turn causes greater fluid displacement (throw distance) within the capillary tube.

Figure 11:
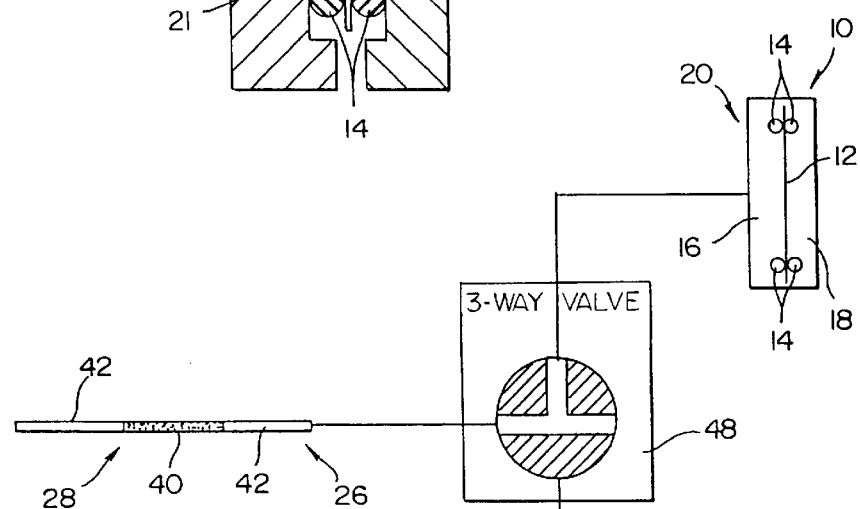
FIG. 11 is a schematic alternate control diagram further including a three-way valve and a shutoff valve to further control aspirated volume within the capillary tube.

Referring to FIGS. 10–11, the invention may include a external control means to vent excess dead air volume and to control aspirated volume within the capillary tube. As shown in FIG. 10, a small pressure release valve 46 is connected to the dead volume within the air sealed space between the piezo-ceramic disk and the end of the capillary tube. This valve allows the fluid volume to be moved away from the end of the capillary before mixing starts. The release valve is opened and closed in concert with the actuator motion so that the pressure of the dead volume is equilibrated through the valve, instead of by fluid motion. For instance, by opening the valve for all actuator displacements that reduce the dead volume and closing it for the dead volume expanding motions, the fluid is moved incrementally toward the actuator and away from the external open end of the capillary. Feed-back from a fluid imaging system (not shown) can be used for precise positioning, if needed.

An additional control system is shown in FIG. 11, where instead of a release valve, a three-way valve 48 is connected to the dead air volume, with one path going to the piezo-ceramic disk, and the other path going to a shut-off valve 50, which is vented.

The present invention also is directed to a method of mixing fluid slugs in a capillary tube through the resonation of a piezo-ceramic disk. The device to hold the piezo-ceramic disk may be like that of the device 10 discussed above.

The illustrated embodiments are only examples of the present invention and, therefore, are non-limitive. It is to be understood that many changes in the particular structure, materials and features of the invention may be made without departing from the spirit and scope of the invention. Therefore, it is the Applicants' intention that its patent rights not be limited by the particular embodiments illustrated and described herein, but rather determined by the following claims, interpreted according to accepted doctrines of claim interpretation, including use of the doctrines of equivalents and reversal of parts.

What is claimed is:

1. A device for mixing aspirated fluid within a capillary tube comprising:

a mounting frame having a first mounting plate and a second mounting plate;

a diaphragm that is positioned between the first and second mounting plates, said diaphragm being deflectable by application of a voltage to said diaphragm;

at least one seal positioned to form an air seal between the diaphragm and at least the first mounting plate;

said first mounting plate including a first opening extending along an axis and sized to receive an end of the aspirated fluid capillary tube such that the received end is essentially perpendicular and adjacent to the diaphragm, and a second smaller opening axially aligned and communicating with said first opening and connecting the air seal between the diaphragm and the first mounting plate and the end of the capillary tube; and a power source to apply a voltage to the diaphragm;

wherein, in use, the end of the aspirated fluid capillary tube is received into the first opening of the first mounting plate such that the fluid is sealed with the air seal between the diaphragm and the first mounting plate, and a voltage is applied to the diaphragm to deflect the diaphragm, such that deflection of the diaphragm rapidly moves the fluid within the capillary tube such that the fluid is mixed in a matter of seconds.

2. The device according to claim 1, wherein the diaphragm is a piezo-ceramic disk.

3. The device according to claim 1, wherein said at least one seal is an O-ring.

4. The device according to claim 1, wherein said first opening extends through a portion of the width of the first mounting plate creating an abutment within the first mounting plate to restrain the received end of the capillary tube.

5. The device according to claim 4, wherein the second opening extends axially of the first opening through the remainder of the width of the first mounting plate to join the air seal between the diaphragm and the first mounting plate to the fluid within the capillary tube.

6. The device according to claim 5, further comprising a seal sealing the capillary tube around the first opening.

7. The device according to claim 5, further comprising a pressure relief valve venting the air sealed space between the diaphragm and the received end of the capillary tube to further externally control the pressure within the capillary tube during mixing.

8. The device according to claim 5, further comprising a three-way valve, and a vented shut-off valves; said three-way valve being connected to the air sealed space between the diaphragm and the received end of the capillary tube and having a first path to the diaphragm and a second path to the shut-off valve in order to selectively connect the air sealed space to the diaphragm and to the shut-off valve.

9. The device according to claim 8, further comprising a protrusion extending from the first mounting plate within the space between the first mounting plate and the second mounting plate, said protrusion being of a size to receive said at least one seal in order to better seal the air seal between the diaphragm and the first mounting plate.

10. The device according to claim 1, further comprising a seal sealing the capillary tube around the first opening.

11. The device according to claim 1, further comprising a plurality of parallel diaphragms, each sandwiched between its own pair of seals, wherein each diaphragm includes its own perpendicularly-oriented second opening that is commonly vented to the received end of the capillary tube to improve fluid displacement within the capillary tube.

12. A method of mixing aspirated fluid within a capillary tube comprising:

providing a capillary tube containing an aspirated fluid slug encased in dead air volume;

providing a diaphragm mixing device having a diaphragm, which is air sealed within a mounting frame, wherein the mounting frame includes an opening of a size to receive an end of said capillary tube;

inserting an end of said capillary tube into said opening such that the inserted end is essentially perpendicular and adjacent to the diaphragm and the dead air volume of the inserted end becomes connected and sealed to air between the diaphragm and the capillary tube end; and applying a voltage to said diaphragm such that the diaphragm resonates asymmetrically to displace the dead air volume, and said fluid slug within said capillary tube rapidly is moved back and forth by the displaced air volume to mix the fluid slug in a matter of seconds.

13. The method according to claim 12, wherein the diaphragm is a piezo-ceramic disk.

14. A device for mixing aspirated fluid within a capillary tube comprising:

a mounting frame having a mounting plate;

a diaphragm carried by the mounting frame and positioned adjacent to the mounting plate, said diaphragm being deflectable by application of a voltage to said diaphragm;

a seal positioned to form an air seal between the diaphragm and the mounting plate;

said mounting plate including a first opening extending along an axis and sized to receive an end of the capillary tube such that said end is essentially perpendicular and adjacent to the diaphragm, and a second smaller opening axially aligned and communicating with said first opening and connecting the air seal between the diaphragm and the mounting plate and said end of the capillary tube; and a power source to apply a voltage to the diaphragm;

wherein, in use, said end of the capillary tube is received into said first opening such that the fluid is sealed with the air seal between the diaphragm and the mounting plate, and a voltage is applied to the diaphragm to deflect the diaphragm, such that deflection of the diaphragm moves the fluid within the capillary tube to mix the fluid.

15. The device according to claim 14, wherein the diaphragm is a piezo-ceramic disk.

16. The device according to claim 14, wherein said first opening extends through a portion of the width of the mounting plate creating an abutment within the mounting plate to restrain the received end of the capillary tube.

17. The device according to claim 16, wherein the second opening extends axially of the first opening through the remainder of the width of the mounting plate to join the air seal between the diaphragm and the mounting plate to the fluid within the capillary tube.

18. The device according to claim 17, further comprising a seal sealing the capillary tube around the first opening.

19. The device according to claim 14, further comprising a seal sealing the capillary tube around the first opening.

20. The device according to claim 14, in which the mounting frame includes a second mounting plate, said seal and a second seal are positioned between said mounting plates, and said diaphragm is sandwiched between said seals.

21. The device according to claim 20, further comprising a third seal sealing the capillary tube around the first opening.

* * * * *

UNITED STATES PATENT AND TRADEMARK OFFICE
CERTIFICATE OF CORRECTION

PATENT NO: 5,890,802

DATED: April 6, 1999

INVENTOR(S): Harold T. Evensen and David L. Cunningham

It is certified that error appears in the above-identified patent and that said Letters Patent is hereby corrected as shown below:

Column 6, line 45, Equation (1):

$$M_f \ddot{x}_1 = (P_{dead} - P_{atm}) \pi R^2 - 2eRL\tau,$$

should be:

$$m_f \ddot{x}_1 = (P_{dead} - P_{atm}) \pi R^2 - 2\pi RL\tau$$

Column 7, line 25, $$\int Q(t) \text{ as } 2\pi \int_0^R \int_0^t u(R,t)$$

should be:

$$\int Q(t) \text{ as } 2\pi \int_0^R \int_0^t u(r,t)$$

Column 7, line 53, Equation (7)

$$P_{dead} - P_{atm} = \frac{P_{atm}(x_{10} - x_{00}) \pi R^2}{(x_1 - x_0) \pi R^2} - P_{atm}$$

should be:

$$P_{dead} - P_{atm} = \frac{P_{atm}(x_{10} - x_{00}) \pi R^2}{(x_1 - x_0) \pi R^2} - P_{atm}$$

$$= P_{atm} \left( \frac{(x_{10} - x_1) - (x_{\infty} - x_0)}{x_1 - x_0} \right)$$

UNITED STATES PATENT AND TRADEMARK OFFICE
CERTIFICATE OF CORRECTION

PATENT NO: 5,890,802

DATED: April 6, 1999

INVENTOR(S): Harold T. Evensen and David L. Cunningham

It is certified that error appears in the above-identified patent and that said Letters Patent is hereby corrected as shown below:

Column 7, line 58, "$m_f = P\pi R^2 L$" should be -- $m_f = p\pi R^2 L$ --.

Column 8, line 8, Equation (10)

$$\omega_n \equiv \frac{P_{aim}\pi R^2}{V_{dead}\rho L}, \quad \zeta \equiv \frac{4\mu}{R^3}\sqrt{\frac{V_{dead}L}{P_{aim}\pi\rho}}.$$

should be:

$$\omega_n^2 \equiv \frac{P_{atm}\pi R^2}{V_{dead}\rho L}, \quad \zeta \equiv \frac{4\mu}{R^3}\sqrt{\frac{V_{dead}L}{P_{atm}\pi\rho}}.$$

UNITED STATES PATENT AND TRADEMARK OFFICE
CERTIFICATE OF CORRECTION

PATENT NO. : 5,890,802

DATED : April 6, 1999

INVENTOR(S) : Harold T. Evensen and David L. Cunningham

It is certified that error appears in the above-identified patent and that said Letters Patent is hereby corrected as shown below:

Column 8, line 18, Equation (11)

$$\omega_{BW}^2 = \omega_n^2(1-2\zeta^2+\sqrt{(2\zeta^2-1)^{2+1}}).$$

should be:

$$\omega_{BW}^2 = \omega_n^2(1-2\zeta^2+\sqrt{(2\zeta^2-1)^2+1}).$$

Claim 8, column 11, line 54, "valves" should be -- valve --.

Signed and Sealed this

Twenty-ninth Day of February, 2000

Q. TODD DICKINSON

*Attest:*

*Attesting Officer*  *Commissioner of Patents and Trademarks*